United States Patent [19]

Spotteck

[11] 4,014,100
[45] Mar. 29, 1977

[54] ELECTRIC TOOTH POLISHER
[75] Inventor: Frederick P. Spotteck, Middle Village, N.Y.
[73] Assignee: The Raymond Lee Organization, Inc., a part interest
[22] Filed: Sept. 15, 1975
[21] Appl. No.: 613,125
[52] U.S. Cl. .................................................. 32/59
[51] Int. Cl.² .......................................... A61C 3/06
[58] Field of Search ........... 222/214, 386; 401/205, 401/206; 32/57, 58, 59

[56] References Cited
UNITED STATES PATENTS

| | | | |
|---|---|---|---|
| 3,389,468 | 6/1968 | Lewis et al. | 32/59 |
| 3,663,113 | 5/1972 | Frain et al. | 401/206 |
| 3,740,853 | 6/1973 | Brahler | 32/59 |

*Primary Examiner*—Robert Peshock

[57] ABSTRACT

Tooth polishing apparatus employs hand held electrically operated means and a polishing head impregnated with a liquid dentifrice rotated by the means. The head is placed in contact with the teeth to be cleaned. The head is generally conically shaped and porous. A shallow hollow cylinder containing dentifrice is secured to the base of the head with a discharge orifice communicating with the base of the head. Normally closed valve means disposed partially in the head and partially in the cylinder normally closes the orifice. When the head is inverted with the apex pointing downward and is pressed upwardly manually, the orifice is opened. The dentrifrice then flows out of the orifice and into the head to impregnate it.

4 Claims, 4 Drawing Figures

ELECTRIC TOOTH POLISHER

SUMMARY OF THE INVENTION

The invention enables a user to polish his teeth thereby producing the same appearance as is normally obtained when the teeth have been polished in a dentist's office by a dentist or dental technician.

To this end, a generally conical shaped sponge like polishing head of about the size of an adult's finger tip is employed. The head is hollow and is porous. The head is rigid, but has an outer resilient coating to avoid injury to teeth where the invention is in use. The orifice communicates with the base of the head. The cylinder is secured to the base of the head. Valve means disposed partially in the head and partially in the cylinder has a normally closed position at which the orifice is sealed. When the head is inverted and the vertex is pressed upward, the orifice is opened and the dentifrice flows downward by gravity through the open orifice into the pores of the head to impregnate same.

Suitable hand held electrically operated means can be used to rotate the head and produce the polishing action.

DETAILED DESCRIPTION OF PREFERRED EMBODIMENTS

Figure 1:
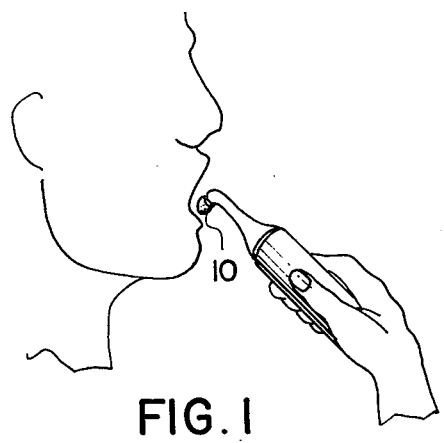
FIG. 1 shows the invention in use.
Figure 2:
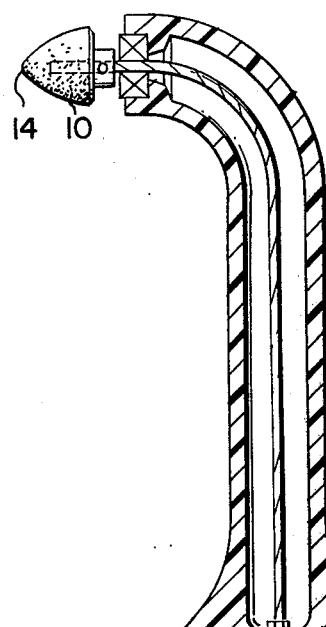
FIG. 2 is a cross sectional view of the hand held electrically operated means.
Figure 3:
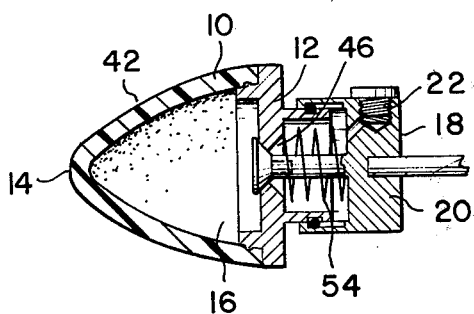
FIG. 3 is a cutaway view of the polishing head with the orifice closed.
Figure 4:
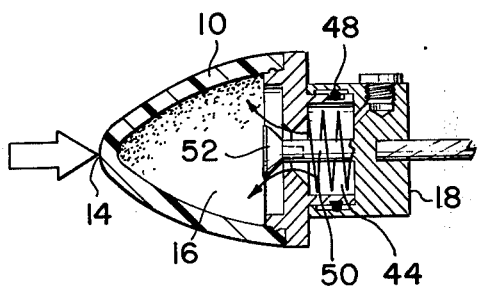
FIG. 4 is a view similar to FIG. 3, but showing the orifice opened.

Referring now to FIGS. 1–4, a generally conically shaped polishing head 10 formed of a rigid material has a base 12, an apex 14 and a hollow interior 16. The wall of the head has pores 40 and has an outer layer 42 with like pores. Layer 42 is a soft resilient material similar to a sponge which prevents injury to the teeth. The head is about as large as the finger tip of an adult.

The base has a centrally disposed orifice 46 in the form of a truncated cone. The base is surmounted by a cylinder 18 which is hollow and contains a conventional liquid dentifrice polishing agent 20 in hollow interior 44. The interior 44 is vented to the atmosphere. The cylinder is made in two halves joined together by O ring seal 48 which are relatively movable. A plunger 50 having a truncated head 52 oppositely disposed in direction to orifice 46 is held by spring 54 to normally close the orifice. When the head is inverted and pressure exerted on the vertex to squeeze the two halves of the cylinder closer together, the plunger head is moved out of sealing engagement with the orifice whereby the dentifrice can flow as previously described.

A hand held electrically operated device includes casing 28, electric motor 30, an elongated tube 32 with a side opening 34 and a flexible shaft 36 which is rotated when the motor operates. The shaft has an exposed tip 38 which snap fits into depression 24 whereby the head can be rotated for polishing.

I claim:
1. Tooth polishing apparatus comprising:
a generally conically shaped hollow rigid porous polishing head, the base of the head having an orifice;
a shallow hollow cylinder having a vent, said cylinder being secured to said base with the orifice communicating with the interior of the cylinder, said cylinder containing a liquid dentifrice;
valve means disposed partially in the head and partially in the cylinder, said means having a normally closed position at which the orifice is sealed, said means opening the orifice to allow the dentifrice to flow into the head and out of the pores when the head is inverted and the head and cylinder are squeezed together; and including a hand held electrically operated means for rotating said head whereby teeth can be polished by the impregnated head.

2. Apparatus of claim 1 wherein said hand held means includes a flexible rotatable shaft having an exposed end, said cylinder having means for detachably engaging the exposes end of the shaft.

3. Apparatus of claim 2 wherein said head has a soft resilient outer layer having pores aligned with the pores in the head itself.

4. Apparatus of claim 3 wherein said means includes a spring loaded shaft having a head with the shape of a truncated cone and the orifice has like shape but is oppositely directed.

* * * * *